United States Patent [19]

Hay et al.

[11] Patent Number: 5,169,923
[45] Date of Patent: Dec. 8, 1992

[54] BISPHENOLS AND POLY(IMIDOARYLETHER KETONE)S AND POLY(IMIDOARYLETHER SULFONE)S PRODUCED THEREFROM

[76] Inventors: Allan S. Hay, 5015 Glencairn Ave., Montreal Quebec H3W 2B3; Marko Strukelj, 495 Prince Arthur Street West, Apt., 33, Montreal, Quebec H2X 1T4, both of Canada

[21] Appl. No.: 798,577

[22] Filed: Nov. 26, 1991

Related U.S. Application Data

[63] Continuation of Ser. No. 704,930, May 23, 1991, Pat. No. 5,110,934.

[51] Int. Cl.$^5$ .............................................. C08G 73/10
[52] U.S. Cl. .................................. 528/322; 528/310; 546/159; 546/171; 546/272; 548/451
[58] Field of Search ............... 528/332, 310, 335, 337, 528/341, 322; 546/159, 171, 272; 548/451

[56] References Cited

U.S. PATENT DOCUMENTS 4,014,899 3/1977 Bowman et al. ..................... 548/451
4,171,369 10/1979 Achini et al. ........................ 424/274
4,418,200 11/1983 Zweifel et al. ...................... 548/451

Primary Examiner—Morton Foelak
Assistant Examiner—Richard L. Jones
Attorney, Agent, or Firm—Swabey Ogilvy Renault

[57] ABSTRACT

Bisphenols having a pendent imide moiety, of formula (I)

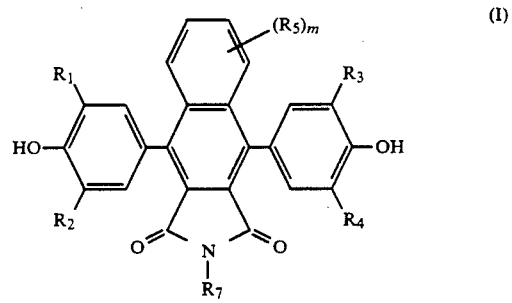

in which $R_1$, $R_2$, $R_3$ and $R_4$, which may be the same or different, are selected from hydrogen, fluorine, chlorine, bromine, alkyl of 1 to 6 carbon atoms, aryl of 6 to 10 carbon atoms, alkoxy of 1 to 6 carbon atoms and aryloxy of 6 to 10 carbon atoms; $R_5$ is selected from fluorine, chlorine, bromine and alkyl of 1 to 6 carbon atoms, and m is 0, 1, 2, 3 or 4; and $R_7$ is alkyl of 1 to 18 carbon atoms, aryl of 6 to 10 carbon atoms, unsubstituted or substituted one or more times by a substituent selected from fluorine, chlorine, trifluoromethyl, alkyl of 1 to 6 carbon atoms, and phenyl, or heteroaryl; are useful in producing poly(imidoarylether ketone)s and poly(-imidoarylether sulfone)s which are amorphous and are soluble in readily available solvents, while displaying high glass transition temperatures and good thermo-oxidative stability.

14 Claims, No Drawings

BISPHENOLS AND POLY(IMIDOARYLETHER KETONE)S AND POLY(IMIDOARYLETHER SULFONE)S PRODUCED THEREFROM

This is a continuation of application Ser. No. 07/704,930, filed May 23, 1991, now U.S. Pat. No. 5,110,934.

BACKGROUND OF THE INVENTION i) Field of the Invention

This invention relates to novel bisphenols having a pendent imide moiety and their preparation, and to poly(imidoarylether) ketones and sulfones produced from the novel bisphenols.

ii) Background of the Invention

Polyimides are synthesized by the reaction of a diamine with a dianhydride, typically this is a two-step reaction route because of the insolubility and infusibility of the resulting polyimide. In the reaction a polyamic acid is formed which is thermally ring-closed to produce the polyimide. Takekoshi T. in Polymer Journal, 1987, 19, 191, describes polyetherimides which overcome these difficulties by using bisphenols such as 4,4'-(1-methylethylidene)bisphenol which introduces flexibility into the polymer chain and provides polymers which are melt processable.

There exists a need for polymers which are soluble in readily available organic solvents and that have high glass transition temperatures and thermo-oxidative stability.

SUMMARY OF THE INVENTION

It is an object of this invention to provide novel bisphenols and their preparation, which bisphenols are useful in preparing novel poly(imidoarylether) ketones, and poly(imidoarylether) sulfones.

It is a further object of this invention to provide novel poly(imidoarylether ketone)s and poly(imidoarylether sulfone)s, and their preparation, which have high glass transition temperatures, are thermo-oxidatively stable, and are soluble in organic solvents.

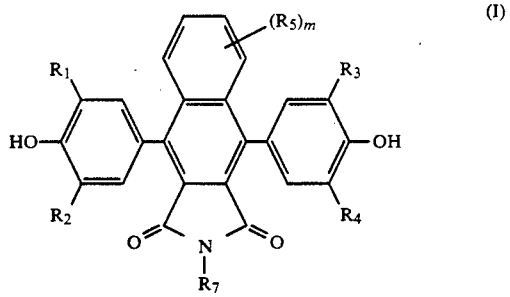

in which $R_1$, $R_2$, $R_3$ and $R_4$, which may be the same or different, are selected from hydrogen, fluorine, chlorine, bromine, alkyl of 1 to 6 carbon atoms, aryl of 6 to 10 carbon atoms, alkoxy of 1 to 6 carbon atoms and aryloxy of 6 to 10 carbon atoms; $R_5$ is selected from fluorine, chlorine, bromine and alkyl of 1 to 6 carbon atoms and m is 0, 1, 2, 3 or 4; and $R_7$ is alkyl of 1 to 18 carbon atoms, aryl of 6 to 10 carbon atoms, unsubstituted or substituted one or more times by a substituent selected from fluorine, chlorine, trifluoromethyl, alkyl of 1 to 6 carbon atoms, and phenyl, or heteroaryl.

In accordance with another aspect of the invention there is provided a process for preparing the bisphenols (I).

In still another aspect of the invention there is provided a polymer of formula (II):

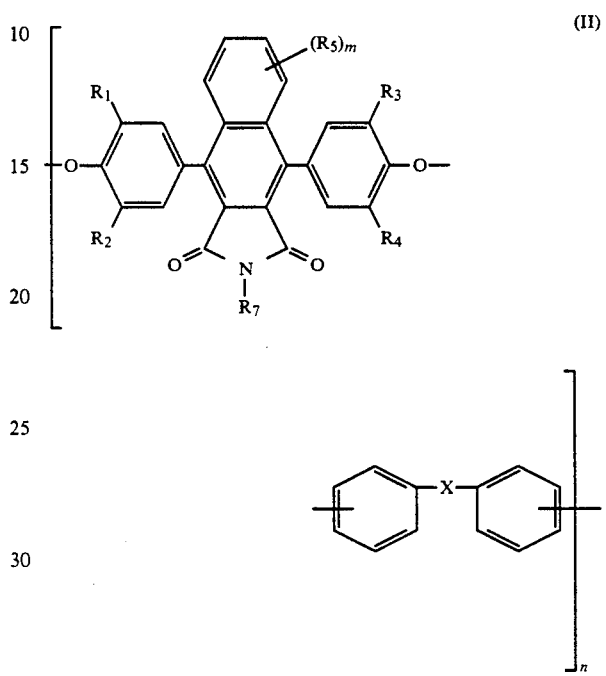

in which $R_1$, $R_2$, $R_3$, $R_4$, $R_5$, $R_7$ and m are as defined above; X is —CO—, —SO$_2$— or —CO—Ar—CO— in which Ar is phenylene; and n is an integer of 2 to 200.

In still another aspect of the invention there is provided a process for preparing the polymers (II).

DESCRIPTION OF PREFERRED EMBODIMENTS i) Bisphenols

The preferred bisphenols (I) are those in which m is 0 such that the benzene ring is unsubstituted and $R_1$, $R_2$, $R_3$ and $R_4$ are all hydrogen. These preferred bisphenols can be produced from phenolphthalein which is readily available.

It is also preferred that $R_1$ and $R_3$ be the same, and that $R_2$ and $R_4$ be the same. The aryl radical and the aryl moiety in the definition of $R_1$, $R_2$, $R_3$, $R_4$ and $R_7$ is preferably phenyl or naphthyl.

The heteroaryl in the definition of $R_7$ is, in particular, pyridinyl or quinolinyl.

When $R_7$ is dodecyl the bisphenol (I) is readily soluble in N-methylpyrrolidone (NMP) at 25° C., while when $R_7$ is phenyl or methyl, moderate temperatures are required to give homogeneous solutions. These temperatures were 60° C. and 80° C., respectively, for the preferred subclass described above.

ii) Preparation of Bisphenols

The preparation of the bisphenols is illustrated in Scheme 1 below for the preferred case in which $R_1$, $R_2$, $R_3$ and $R_4$ are all hydrogen and m is 0. In such case, the reaction scheme as illustrated commences with phenolphthalein (III) which is readily available.

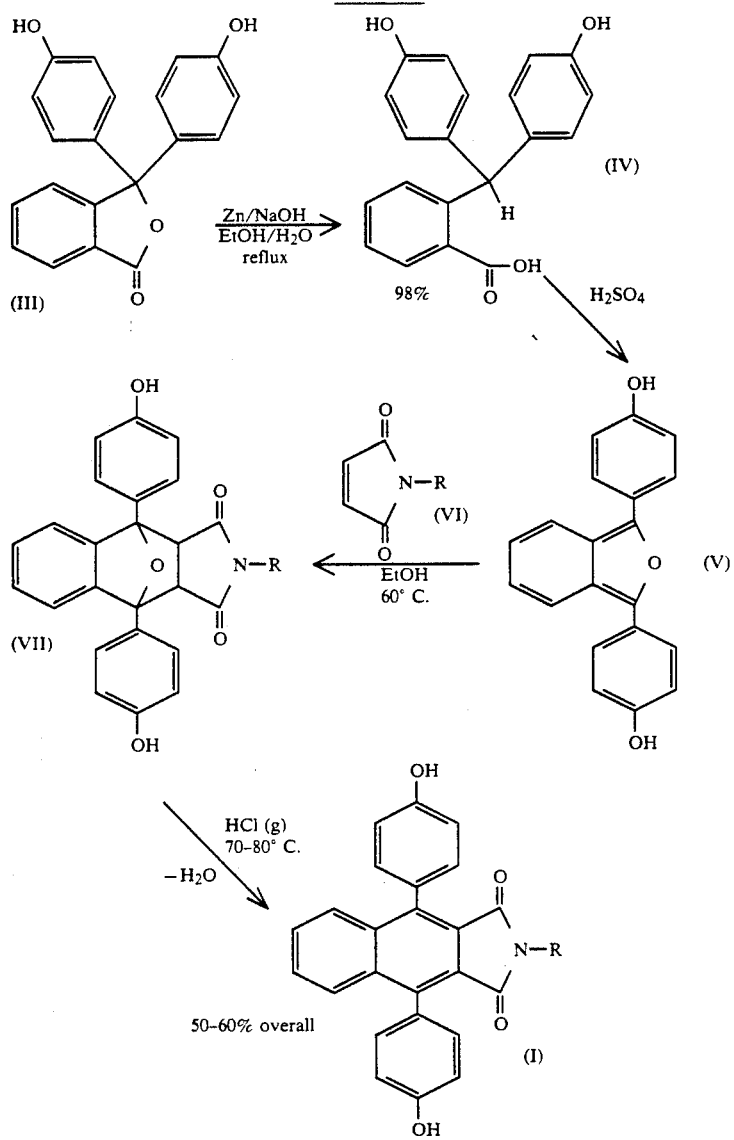

The overall process commencing with phenolphthalein may be considered a three-step sequence rather than a four-step sequence, since the last two steps can be carried out in one pot.

In Scheme 1 the phenolphthalein (III) is reduced to phenolphthalin (IV) employing the procedure of Blicke, F. F.; Patelski, R. A., in J. Am. Chem. Soc., 1936, 58, 274, with zinc and sodium hydroxide in aqueous ethanol under reflux. This reaction proceeds efficiently to yields in excess of 95%. The phenolphthalin (IV) is rearranged in concentrated sulfuric acid to the isobenzofuran (V) using a modified procedure of Blicke and Weinkauf, J. Am. Chem. Soc., 1934, 54, 1454.

The isobenzofuran (V) is reacted with a maleimide (VI) under Diels-Alder conditions, typically in ethanol at moderate elevated temperatures, for example about 60° C.; and the reaction product (VII) is dehydrated, for example with gaseous hydrogen chloride at a temperature of 70-80° C. to produce the bisphenol (I).

In the general reaction the phenolphthalein (III) is replaced by a compound of formula (VIII):

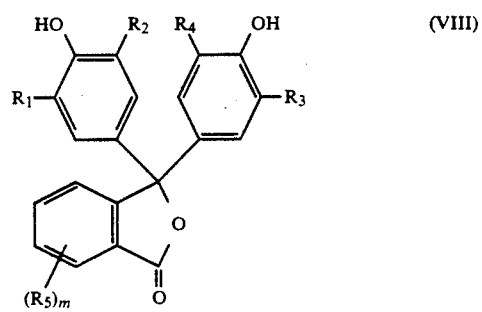

in which $R_1$, $R_2$, $R_3$, $R_4$, $R_5$ and m are as defined above, and is reduced to a compound of formula (IX):

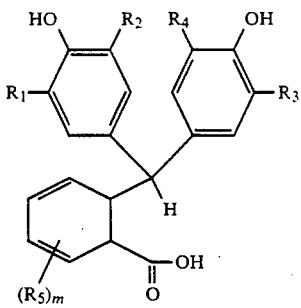

(IX)

in which $R_1$ to $R_5$ and m are as defined above.

Thus the process of the invention contemplates reacting a compound of formula (X):

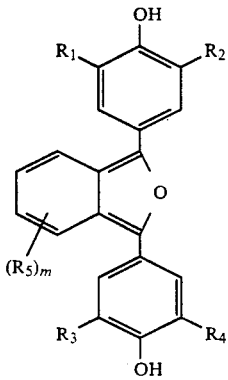

(X)

in which $R_1$, $R_2$, $R_3$, $R_4$, $R_5$ and m are as defined above, with the maleimide (VI) as defined above and dehydrating the Diels-Alder adduct (XI):

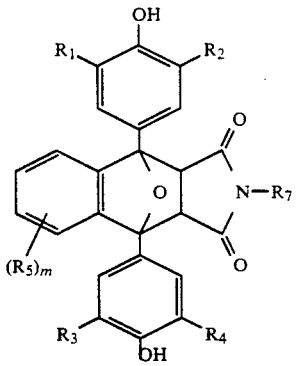

(XI)

in which $R_1$, $R_2$, $R_3$, $R_4$, $R_5$, $R_7$ and m are as defined above to produce the bisphenol (I).

iii) Polymer Synthesis

The polymerization of the bisphenols (I) to produce the polymers (II) is illustrated in Scheme 2 below for the preferred case in which $R_1$, $R_2$, $R_3$ and $R_4$ are all hydrogen, and m is 0. The polymerization is suitably carried out with 4,4'-dihalobenzophenone, 4,4'-dihalodiphenylsulfone or 1,3-bis-(4-halobenzoyl)benzene in which the halo is fluoro or chloro, preferably fluoro. The polymerization is suitably carried out in a solvent, for example N-methylpyrrolidone, dimethylsulfoxide or sulfolane, in the presence of an excess of anhydrous potassium carbonate; the choice of solvent depends on the solubility characteristics of the resulting polymers and appropriate solvents can readily be determined by routine experiments.

SCHEME 2

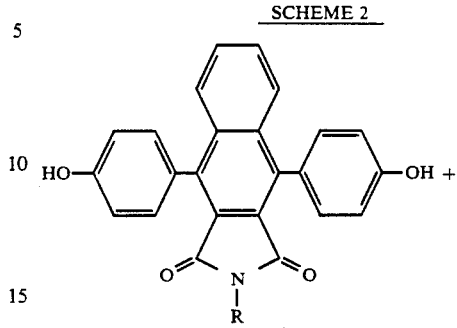

Furthermore, when $R_7$ is methyl, high molecular weight polymers can not be synthesized with difluorobenzophenone and difluorodiphenylsulfone when the solvent is N-methylpyrrolidone because oligomers rapidly precipitate from the reaction solution during the polymerization. High molecular weight polymers can be synthesized when sulfolane is the solvent.

The integer n is a measure of the degree of polymerization and usually will be in the preferred range of 100 to 150.

iv) Polymers

Depending on the value of X the polymers of the invention are characterized as poly(imidoarylether ketone)s or poly(imidoarylether sulfone)s.

In agreement with the solubility characteristics of the parent bisphenols (I), the $R_7$ group has a dramatic effect on the solubility of the resulting polymer.

When $R_7$ is dodecyl, for example, all the polymers are amorphous and readily soluble in chloroform and methylene chloride at room temperature. On the other hand when $R_7$ is, for example, phenyl or methyl, the polymers are less soluble in chloroform and the poly(imidoarylether ketone)s dissolve only in certain dipolar aprotic solvents.

Table 1 below provides a compilation of chemical properties and solubilities of polymers (II) for different values of $R_7$ for the preferred case in which $R_1$, $R_2$, $R_3$ and $R_4$ are all hydrogen and m is 0.

polymer in which $R_7$ is phenyl, failed to reveal a melting point Tm for either polymer.

The polymers in which $R_7$ is phenyl displayed the highest thermo-oxidative stability while those in which $R_7$ is methyl and dodecyl are lower by 45–65° C. and 90–100° C., respectively.

Table 2 below identifies the inherent viscosities, molecular weights obtained by gel permeation chromatog-

TABLE 1

THERMAL PROPERTIES OF POLYMERS

| $R_7$ | Ar | Polymerization Solvent | Tg (C.)* | TGA (C.)** air | TGA (C.)** N2 | Solubility |
|---|---|---|---|---|---|---|
| Methyl | Benzophenone | Sulfolane | 283*** | 525 | 516 | Sulfolane |
|  | Diphenyl Sulfone | Sulfolane | 314 | 503 | 506 | $CHCl_3$ and TCE |
|  | 1,3-Dibenzoyl benzene | NMP | 251 | 524 | 515 | $CHCl_3$ |
| Dodecyl | Benzophenone | NMP | 147 | 482 | 491 | $CHCl_3/CH_2CL_2$ |
|  | Diphenyl Sulfone | NMP | 167 | 471 | 471 | $CHCl_3/CH_2CL_2$ |
|  | 1,3-Dibenzoyl benzene | NMP | 140 | 489 | 487 | $CHCl_3/CH_2CL_2$ |
| Phenyl | Benzophenone | DMSO | 275 | 551 | 561 | $CHCl_3$ |
|  | Diphenyl Sulfone | NMP | 310 | 556 | 550 | $CHCl_3$ (hot) |
|  | 1,3-Dibenzoyl benzene | NMP | 245 | 568 | 566 | $CHCl_3/CH_2CL_2$ |

*DSC. Heating rate 10° C./min
**TGA. Heating rate 10° C./min. Values correspond to the temperature at which a 10% weight loss occurs
***Low molecular weight With reference to Table 1, it can be seen that the highest glass transition temperatures Tg are obtained for polymers in which $R_7$ is methyl, presumably because the polymer chain is most rigid when $R_7$ is methyl. When $R_7$ is phenyl, the Tg's are very close to those when $R_7$ is methyl and the solubility of the polymers is much improved.

When $R_7$ is dodecyl the Tg's are much lower, and in such case the long alkyl chain $R_7$ likely functions as an internal plasticizer.

For a given $R_7$ the poly(imidoarylether sulfone)s have the highest Tg, while the poly(imidoarylether bisketone)s exhibit the lowest Tg.

All of the polymers were amorphous. Attempts were made to induce some degree of crystallinity by holding the ketone polymers in which $R_7$ was phenyl and dodecyl, for 5 hours above their respective Tg's, followed by cooling to 25° C. Subsequent heating to 300° C. for the polymer in which $R_7$ is dodecyl, and 400° C. for the raphy using polystyrene standards, and the film color and characteristics of the preferred class of polymers of Table 1.

TABLE 2

POLYMER VISCOSITIES AND SOLUTION PROPERTIES

| $R_7$ | Ar | Inherent Viscosity* | Film Color | Solvent for Solution Casting | GPC*** Mw × 10⁵ | GPC*** M × 10⁵ | P.D. |
|---|---|---|---|---|---|---|---|
| Methyl | Benzophenone | — | — | — | — | — | — |
|  | Diphenyl Sulfone | 0.64** | Clear and Colourless | TCE | 40 | 16 | 2.5 |
|  | 1,3-Dibenzoyl benzene | 0.62 | Tan | $CHCl_3$ | 48 | 20 | 2.4 |
| Phenyl | Benzophenone | 0.52 | Light Brown | NMP | — | — | — |
|  | Diphenyl Sulfone | 0.91 | Tan | NMP | 90 | 31 | 2.9 |
|  | 1,3-Dibenzoyl benzene | 1.24 | Clear and Light Gold | $CH_2Cl_2$ | 192 | 62 | 3.1 |
| Dodecyl | Benzophenone | 1.1 | Clear and Light Yellow | $CH_2Cl_2$ | 88 | 29 | 3.1 |
|  | Diphenyl Sulfone | 0.55 | Clear and Colourless | $CH_2Cl_2$ | 53 | 22 | 2.4 |
|  | 1,3-Dibenzoyl benzene | 0.9 | Clear and Colourless | $CH_2Cl_2$ | 118 | 48 | 2.5 |

*NMP at 60.7° C.
**TCE at 25.1° C.
***Based on Polystyrene Standards

All of the polymers in Table 2 except the ketone polymer in which $R_7$ is methyl are of high molecular weight and produce tough, flexible films which withstand two 180 degree folds.

Comparing the poly(imidoarylether sulfone) (I) in which $R_7$ is phenyl and $R_1$ to $R_6$ have he preferred values of Tables 1 and 2, with a comparison poly(arylether sulfone) produced with 4,4'-biophenol as the bisphenol, it is found that the polymer of the invention has a glass transition temperature of about 80° C. higher than the Tg of 230° C. of the comparison polymer, and additionally has a higher thermooxidative stability suffering a 10% reduction in weight when heated at a rate

EXAMPLES

Synthesis of Maleimides

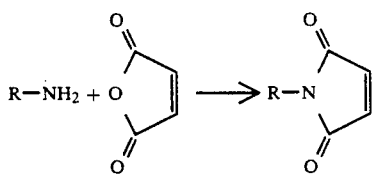

Procedure A. Two Step Synthesis

Example 1.

N-Dodecylmaleimic acid. To a 1000 mL beaker containing 37.8 g (0.204 mol) of dodecylamine in 150 mL of cyclohexane was added 20 g (0.204 mol) of maleic anhydride. The mixture was warmed to 60° C. to dissolve all of the solids and 2 drops of conc. sulfuric acid was added. After 2 hrs. the mixture had deposited a fine white precipitate which was filtered, washed with petroleum ether (50 mL×5), and dried by suction. Yield=98%. m.p.=92° C.

N-Dodecylmalemide. 70.8 g (0.25 mol) of the amic aid was added to a dry 1L round bottom flask containing 600 mL of methyl ethyl ketone (MEK). 52.2 mL (0.375 mol) of dry triethylamine was added dropwise (N.B. most of the amic acid dissolves when the amine is added). 35.4 mL (0.375 mol) of acetic anhydride was added slowly in a dropwise manner while the temperature was increased to 60° C. After 22 hrs. the temperature was reduced to 23° C., and the contents were poured into 2 L of water this was stirred overnight, filtered and dried by suction leaving a tan solid. Weight 66.8 g. Yield=96%. m.p.=47–51° C. This was used without further purification.

Procedure B. One Step Synthesis

Synthesis of Maleimides with substituents on the pendent phenyl group. These maleimides were synthesized in one pot by reacting the appropriate amine with amaleic anhydride in adipolar aprotic solvent (NMP, DMAc, or DMF) to form the amic acid, which was further dehydrated using a catalytic amount of Ni-(OAc(2-H2O or NaOAc and acetic anhydride. For N-(4-t-Butyl)pehnyl maleimide, N-(4-chloro)phenyl maleimide, N-(2-Fluoro)phenyl maleimide, N-(4-Fluoro)phenyl maleimide, N-(2-Phenyl)phenyl maleimide, N-(2-trifluoromethyl)phenyl maleimide, and N-(4-trifluoromethyl)phenyl maleimide the following general procedure was used:

To a dry 500 mL round bottom blask at 0° C. containing 0.168 mol of the aniline and 100 mL dry dipolar aprotic solvent (DMAc or NMP) was added 0.168 mol of maleic anhydride all at once. After 5 min. an additional 45 mL of NMP was added. The contents were stirred at 0° C. for about 1 hour and then allowed to warm to room temperature. After 3 hrs. 0.216 g of Ni-(OAc)$_2$.H$_2$O and 0.575 mol. of acetic anhydride were added. The mixture was normally stirred for 24–48 hours, and then passed through a 0.5 cm plug of alumina into 1L of H$_2$O. If the solids precipitated they were filtered and dried by suction. If the solids did not precipitate, the organic layer was extracted with a suitable solvent (100 mL×5), the combined extracts were washed with brine (200 mL×2), H$_2$O (200 mL×2), dried over MgSO4 and conc. in vacuo. If DMAc remained it was removed by distillation under reduced pressure. N-(2-Fluoro)phenyl maleimide, N-(4-Fluoro)-phenyl maleimide, N-(4-chlorophenyl)maleimide, and N-(4-trifluoromethyl)phenyl maleimide precipitate when poured into water. N-(2)-Phenyl)phenyl maleimide, and N-(2-trifluoromethyl)phenyl maleimide were extracted from the reaction mixture with EtOAc an EtOEt, respectively. The solids were purified by flash column chromatography through silica gel using petroleum ether: EtOAc (3:1) and petroleum ether/EtOEt (4:1), respectively. For N-(3-trifluoromethyl)phenyl maleimide the same conditions as above were applied except dry DMF was used as solvent, and a catalytic amount of fused NaOAc and 1.4 equiv. of acetic anhydride were used. CHCl3 was used to extract the organic layer. Purification was achieved by flash column chromatography (Pet. eter :EtOAc, 8:1).

| | Synthesis of Maleimides from Maleic Anhydride and an Amine | | | | | | | |
|---|---|---|---|---|---|---|---|---|
| | R | Procedure | Solvent | Temp (°C.) | Time (hrs) | Yield (%) | m.p. | Appearance |
| Example 1 | Dodecyl | A | MEK | 60 | 22 | 96 | 92 | Light brown powder |
| Example 2 | 2-Fluorophenyl | B | DMAc | 23 | 24 | 64 | 55–59 | Yellow crystals |
| Example 3 | 4-Fluorophenyl | B | DMAc | 23 | 36 | 81 | 153–155 | Yellow needles |
| Example 4 | 4-Chlorophenyl | B | DMAc | 60 | 29 | 82 | 115–117 | Yellow needles |
| Example 5 | 4-t-Butylphenyl | B | NMP | 23 | 40 | 58 | 95–96 | Yellow needles |
| Example 6 | 3-Trifluoromethylphenyl | B | DMF | 50 | 48 | 41 | oil | Orange |
| Example 7 | 4-Trifluoromethylphenyl | B | DMAc | 23 | 80 | 61 | 151–153 | White powder |

Synthesis of Bisphenols

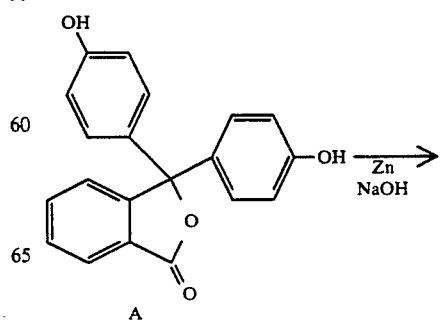

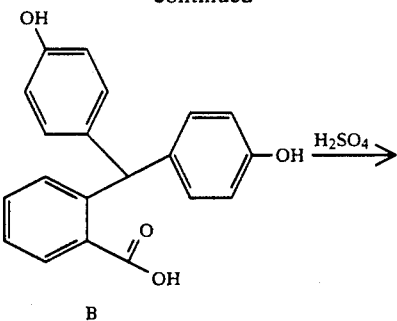

B

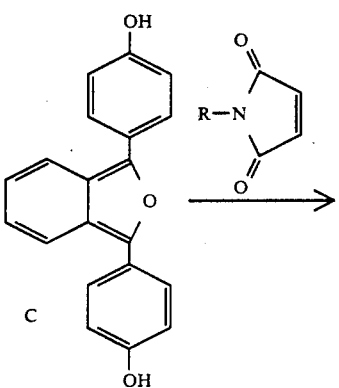

C

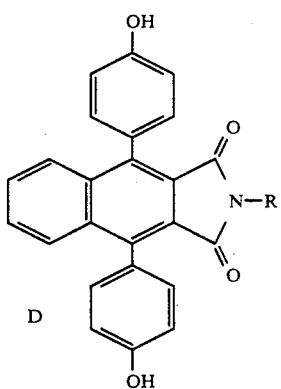

D

Phenolphthaln (B)

To a 3L 3-necked flask containing 60 g of phenolphthalein (A), 450 mL of water and 525 mL of ethanol was added 450 mL of 50% sodium hydroxide solution in ethanol and 300 g of zinc powder. The contents were heated to reflux and maintained at that temperature for 12 hrs. The solution was cooled to room temperature, filtered and acidified until phenolphthalin precipitated as a white powder. This was collected by filtration and dried at 80° C. for 24 hrs. at reduced pressure. Yield=95%. m.p.=234-236° C.

Isobenzofuran (C)—Typical procedure

To a dry 250 mL round bottom flask equipped with a mechanical stirrer containing 20 g (0.062 mol) of phenolphthalin at 0° C. was added, with stirring, 25 mL of conc. sulfuric acid (cooled to 0° C.) This mixture was stirred slowly for 2-3 min. and poured into a 1L beaker containing 600 mL of ice-water. To retrieve the remaining solids there was added cold water (~20-30 mL×4) while a spatula was used to scrape out the remainder. The solids were combined. The green solid was then filtered, washed with 1 L of cold water and dried for 15-20 min. before being used in the Diels-Alder reaction.

Bisaryl(imido)phenol (D)

To a 500 mL round bottom flask containing 0.069 mol N-(methyl) maleimide in 200 mL of absolute ethanol was added the isobenzofuran generated above. The mixture was heated to 80-90° C., After 15-20 min. the Diels-Alder reaction was complete as indicated by thin layer chromatography and a change in color from red and clear to light brown and clear. This product was not isolated, since the Diels-Alder reaction is accompanied by some dehydration which has already occurred due to the presence of residual sulfuric acid from the acid catalyzed rearrangement above.

To the mixture of products from the Diels-Alder reaction was added HCl(g), while maintaining the temperature at between 70-90° C. Complete dehydration usually occurred in about 1-2 hrs.

| Bisphenols from Phenolphthalin | | | | |
|---|---|---|---|---|
| | R group | Yield | m.p. | Appearance |
| Example 8 | Dodecyl | 50-60 | 255 | Yellow needles |
| Example 9 | Methyl | 50-60 | 410 | Yellow needles |
| Example 10 | Phenyl | 50-60 | 392 | Yellow needles |
| Example 11 | 2-Fluorophenyl | 46 | 374-6 | Yellow needles |
| Example 12 | 4-Fluorophenyl | 51 | 367 | Yellow needles |
| Example 13 | 4-Chlorophenyl | 47 | 156-158 | Yellow needles |
| Example 14 | 3-Trifluoromethylphenyl | 62 | 362 | Yellow needles |
| Example 15 | 4-Trifluoromethylphenyl | 43 | 360 | Yellow powder |
| Example 16 | 2-Phenylphenyl | 40 | 329-31 | White crystals |

The precipitated product was filtered and dried. Yield=50-60%.

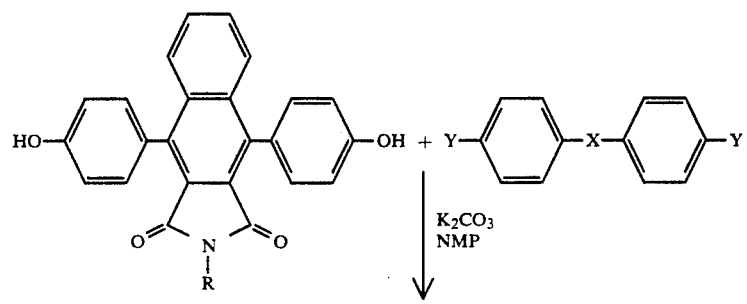

-continued

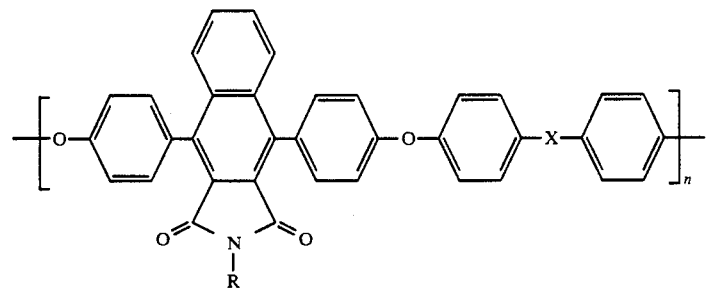

Y = F or Cl
A: X = SO₂
B: X = CO

C: X = 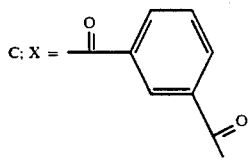

Recrystallization from acetic acid yielded monomer pure enough for polymerization. When the electron withdrawing group on the ring is F or CF3 complete dehydration occurs by stirring overnight at 70-90° C., Hcl(g) is not required.

Polymer Synthesis

Typical Procedure

To a dry 50 mL 3-neck flask equipped with a 2.5 cm Teflon stirring bar, a Dean-Stark trap (filled with toluene), a cold water condenser, a thermometer and nitrogen inlet was added 0.860 g (1.88 mmol) of N-Phenyl-(imido)bisphenol and 0.605 g (1.88 mmol) of 1,3-bis(4-flurobenzoyl)benzene. 3.7 mL of toluene was used to wash down any remaining solids stuck to the mouth of the flask and 7.3 mL of NMP was added. The contents were warmed to 40° C. and 0.346 g (2.632 mmol-40% excess) of anhydrous potassium carbonate was added. The temperature was increased to reflux (130° C.). To insure complete dehydration refluxing was continued between 130° C. and 140° C. for two to three hours, at which time the temperature was slowly increased to 160-165° C. over about 3 hours (a significant increase in viscosity is apparent at 150° C.). Reaction at this temperature was continued until the reaction mixture could no longer be stirred or the polymer began to precipitate from solution. The reaction was diluted with 15-20 mL of NMP, filtered hot through Celite to remove the salts and precipitated dropwise into a vigorously stirred solution of methanol/water (300 mL : 200 mL, respectively). Filtration, drying, redissolved in 40 mL of chloroform and precipitation a second time in methanol yielded a white fibrous polymer after filtration. Drying at 80° C. under vacuum for 24 hours gave a 70% yield of white fibrous polymer.

| | R | X | Polymerization Solvent | Inherent Viscosity | Tg (°C.)* | TGA (°C.)** air | TGA (°C.)** N2 | Solubility | Young's Modulus at 23° C. (GPa) |
|---|---|---|---|---|---|---|---|---|---|
| Example 17 | Methyl | B | Sulfolane | — | 283 | 525 | 516 | Sulfolane | — |
| Example 18 | | A | Sulfolane | 0.64 | 314 | 503 | 506 | CHCl3 and TCE | 2.5 |
| Example 19 | | C | NMP | 0.62 | 251 | 524 | 515 | CHCL3 | 2.4 |
| Example 20 | Dodecyl | B | NMP | 1.1 | 147 | 482 | 491 | CHCL3/CH2CL2 | 2.6 |
| Example 21 | | A | NMP | 0.55 | 167 | 471 | 471 | CHCL3/CH2CL2 | 2.6 |
| Example 22 | | C | NMP | 0.9 | 140 | 489 | 487 | CHCL3/CH2CL2 | 2.7 |
| Example 23 | Phenyl | B | DMSO | 0.52 | 275 | 551 | 561 | CHCl3 | 2.5 |
| Example 24 | | A | NMP | 0.91 | 310 | 556 | 550 | CHCl3 (hot) | 2.6 |
| Example 25 | | C | NMP | 1.24 | 245 | 568 | 566 | CHCL3/CH2CL2 | 2 |
| Example 26 | 4-Chlorophenyl | B | NMP | 0.71 | 272 | 550 | 564 | CHCl3 | 2.8 |
| Example 27 | | A | NMP | 0.55 | 280 | 539 | 552 | CHCl3 | 2.9 |
| Example 28 | 2-Phenylphenyl | A | NMP | — | 278 | 547 | 539 | TCE | 2 |
| Example 29 | 2-Fluorophenyl | B | NMP | — | 282 | 560 | 565 | TCE | 1.4 |
| Example 30 | | A | NMP | — | — | 549 | 540 | TCE | 3.4 |
| Example 31 | 4-Fluorophenyl | B | NMP | 1.07 | 290 | 560 | 578 | NMP | 0.8 |
| Example 32 | | A | NMP | 0.69 | 300 | 558 | 555 | CHCl3 | 2.6 |
| Example 33 | | C | NMP | 0.71 | 243 | 572 | 572 | CHCl3 | 2.8 |
| Example 34 | 3-Trifluoromethylphenyl | B | NMP | 0.65 | 252 | 561 | 569 | TCE | 3 |
| Example 35 | | A | NMP | 0.63 | 282 | 550 | 550 | CHCl3 | 2.3 |
| Example 36 | 4-Trifluoromethylphenyl | B | NMP | 0.84 | 260 | 552 | 573 | TCE | 2 |
| Example 37 | | A | NMP | 0.56 | 290 | 540 | 542 | CHCl3 | 1.7 |

*DSC
**Temperature for 10% weight loss

Film Casting

Polymer films were cast from chloroform or sym-tetrachloroethane. For example, 130 mg of polymer was dissolved in 2-3 mL chloroform and evaporated slowly at room temperature (12-24 hours) to yield a tough and flexible film (Thickness=0.070-0.120 mm). For sym-tetrachloroethane, solutions were cast in a forced air oven at 108° C. (12-24 hours).

We claim:

1. A polymer of formula (II):

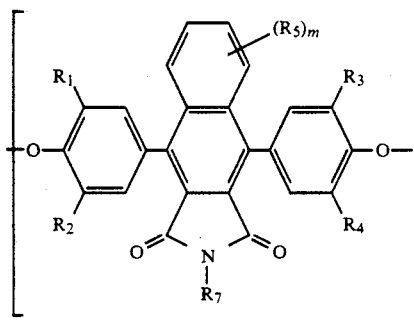

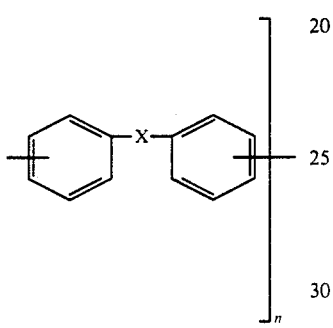

in which $R_1$, $R_2$, $R_3$ and $R_4$, which may the same or different, are selected from the group consisting of hydrogen, fluorine, chlorine, bromine, alkyl of 1 to 6 carbon atoms, aryl of 6 to 10 carbon atoms, alkoxy of 1 to 6 carbon atoms and aryloxy of 6 to 10 carbon atoms;

$R_5$ is selected from the group consisting of fluorine, chlorine, bromine and alkyl of 1 to 6 carbon atoms, m is 0, 1, 2, 3 or 4, $R_7$ is alkyl of 1 to 18 carbon atoms; aryl of 6 to 10 carbon atoms, unsubstituted or substituted one or more times by a substituent selected from the group consisting of fluorine, chlorine, trifluoromethyl alkyl of 1 to 6 carbon atoms and phenyl; or heteroaryl;

X is —CO—, —SO$_2$— or —CO—Ar—CO— in which Ar is phenylene, and n is an integer of 2 to 200.

2. A polymer of claim 1 in which $R_1$, $R_2$, $R_3$ and $R_4$ are all hydrogen, m is 0; and X is —CO— and para to the phenol oxygens of the polymer chain.

3. A polymer of claim 2 in which $R_7$ is methyl, dodecyl, phenyl or phenyl substituted by fluoro, chloro, trifluoromethyl, t-butyl or phenyl.

4. A polymer of claim 1, in which $R_1$, $R_2$, $R_3$ and $R_4$ are all hydrogen, m is 0, and X is —SO$_2$— and para to the phenolic oxygens of the polymer chain.

5. A polymer of claim 4 in which $R_7$ is methyl, dodecyl, phenyl or phenyl substituted by fluoro, chloro, trifluoromethyl, t-butyl or phenyl.

6. A polymer of claim 1 in which $R_1$, $R_2$, $R_3$ and $R_4$ are all hydrogen, m is 0; and X is -CO-Ar-CO wherein Ar is 1,3-phenylene.

7. A polymer of claim 6 in which $R_7$ is methyl, dodecyl, phenyl or phenyl substituted by fluoro, chloro, trifluoromethyl, t-butyl or phenyl.

8. A process for producing a polymer of formula (II):

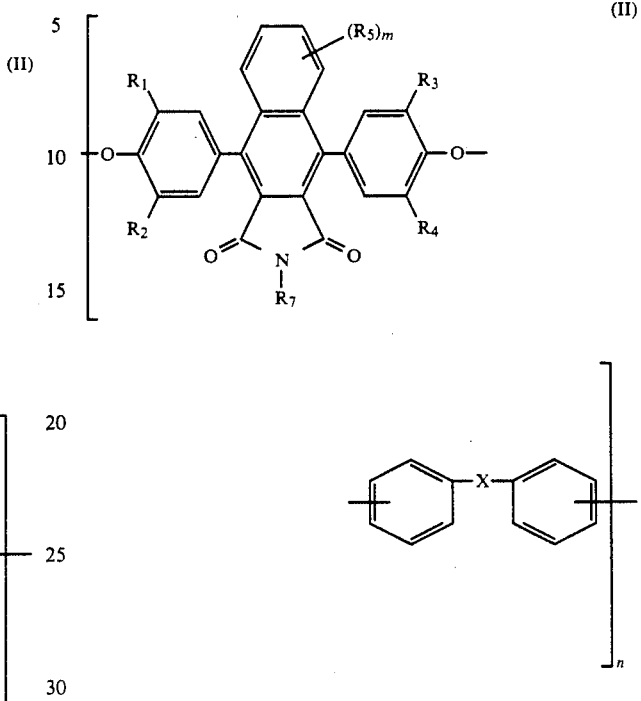

in which $R_1$, $R_2$, $R_3$ and $R_4$, which may be the same or different, are selected from the group consisting of hydrogen, fluorine chlorine, bromine, alkyl of 1 to 6 carbon atoms, aryl of 6 to 10 carbon atoms, alkoxy of 1 to 6 carbon atoms and aryloxy of 6 to 10 carbon atoms;

$R_5$ is selected from the group consisting of fluorine, chlorine, bromine and alkyl of 1 to 6 carbon atoms, m is 0, 1, 2, 3 or 4, $R_7$ is alkyl of 1 to 18 carbon atoms; aryl of 6 to 10 carbon atoms, unsubstituted or substituted one or more times by a substituent selected from the group consisting of fluorine, chlorine, trifluoromethyl alkyl of 1 to 6 carbon atoms and phenyl; or heteroaryl;

X is —CO—, —SO$_2$— or —CO—Ar—CO— in which Ar is phenylene, and n is an integer of 2 to 200; comprising polymerizing a bisphenol of formula (I):

wherein said polymerizing is carried out at 160 to 180 C. in a solvent in the presence of anhydrous potassium carbonate.

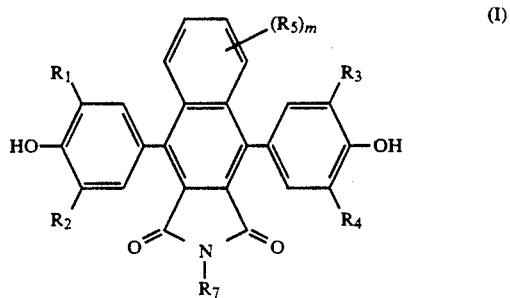

in which $R_1$ to $R_5$, $R_7$ and m are as defined above, with a compound of formula (XII):

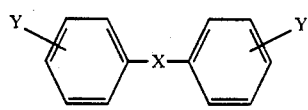 (XII)

in which Y is fluoro or chloro, and X is —CO—, —SO$_2$— or

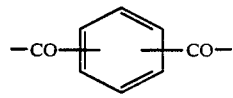

9. A process according to claim 8 in which said compound of formula (XII) is 4,4'-difluorobenzophenone.

10. A process according to claim 8 in which said compound of formula (XII) is 4,4'-difluorodiphenyl sulfone.

11. A process according to claim 8 in which said compound of formula (XII) is 1,3-bis-(4-fluorobenzoyl)-benzene.

12. A process according to claim 9 in which $R_1$, $R_2$, $R_3$ and $R_4$ are all hydrogen, and m is 0.

13. A process according to claim 10 in which $R_1$, $R_2$, $R_3$ and $R_4$ are all hydrogen, and m is 0.

14. A process according to claim 11 in which $R_1$, $R_2$, $R_3$ and $R_4$ are all hydrogen, and m is 0.

* * * * *